(12) United States Patent
Seeber

(10) Patent No.: US 7,251,521 B2
(45) Date of Patent: Jul. 31, 2007

(54) MOTION SENSING MRI LOCAL COIL

(75) Inventor: Derek Seeber, Wauwatosa, WI (US)

(73) Assignee: IGC Medical Advances, Inc., Milwaukee, WI (US)

( * ) Notice: Subject to any disclaimer, the term of this patent is extended or adjusted under 35 U.S.C. 154(b) by 571 days.

(21) Appl. No.: 10/716,635

(22) Filed: Nov. 19, 2003

(65) Prior Publication Data

US 2005/0107685 A1    May 19, 2005

(51) Int. Cl.
*A61B 5/05* (2006.01)
(52) U.S. Cl. .................. 600/422; 600/407; 600/410; 600/421; 600/425
(58) Field of Classification Search ............... 600/422, 600/415, 421, 595, 410, 407; 324/307, 309, 324/321, 318
See application file for complete search history.

(56) References Cited

U.S. PATENT DOCUMENTS

| | | | | |
|---|---|---|---|---|
| 3,527,106 | A * | 9/1970 | Hirtreiter | 73/514.19 |
| 5,477,144 | A * | 12/1995 | Rogers, Jr. | 600/413 |
| 5,977,769 | A * | 11/1999 | Bornert et al. | 324/306 |
| 6,148,229 | A * | 11/2000 | Morris et al. | 600/509 |
| 7,034,533 | B2 * | 4/2006 | Mugler et al. | 324/318 |
| 2002/0118373 | A1* | 8/2002 | Eviatar et al. | 356/614 |
| 2004/0051527 | A1* | 3/2004 | Mugler, III et al. | 324/309 |
| 2005/0054939 | A1* | 3/2005 | Ben-Ari et al. | 600/506 |

* cited by examiner

*Primary Examiner*—Brian L. Casler
*Assistant Examiner*—James Kish
(74) *Attorney, Agent, or Firm*—Boyle Fredrickson Newholm Stein & Gratz S.C.

(57) ABSTRACT

A motion sensing MRI coil allows correction of motion-induced image artifacts by the MRI machine or on a machine independent basis using correction circuitry associated with the coil.

17 Claims, 2 Drawing Sheets

MOTION SENSING MRI LOCAL COIL

CROSS-REFERENCE TO RELATED APPLICATIONS

STATEMENT REGARDING FEDERALLY SPONSORED RESEARCH OR DEVELOPMENT

BACKGROUND OF THE INVENTION

The field of the invention is magnetic resonance imaging (MRI) and, in particular, local coils for use in MRI.

In MRI, a uniform magnetic field $B_0$ is applied to an imaged object along the z-axis of a Cartesian coordinate system fixed with respect to the imaged object. The effect of the magnetic field $B_0$ is to align the object's nuclear spins along the z-axis.

In response to a radio frequency (RF) excitation signal of the proper frequency oriented within the x-y plane, the nuclei precess about the z-axis at their Larmor frequencies according to the following equation:

$$\omega = \gamma B_0 \qquad (1)$$

where $\omega$ is the Larmor frequency, and $\gamma$ is the gyromagnetic ratio which is a constant and a property of the particular nuclei. The value of the gyromagnetic ratio $\gamma$ or protons is 42.5759 MHz/Tesla.

In a typical imaging sequence for an axial slice, an RF excitation signal having a frequency centered at the Larmor frequency of the protons is applied to the imaged object at the same time as a magnetic field gradient $G_z$ is applied. The gradient field $G_z$ causes only the nuclei in a slice with a limited width through the object along an x-y plane to be excited into resonance.

After the excitation of the nuclei in this slice, magnetic field gradients are applied along the x- and y-axes. The gradient along the x-axis, $G_x$, causes the nuclei to process at different frequencies depending on their position along the x-axis, that is, $G_x$ spatially encodes the precessing nuclei by frequency. The y-axis gradient, $G_y$, is incremented through a series of values and encodes the y position into the rate of change of phase of the precessing nuclei as a function of gradient amplitude, a process typically referred to as phase encoding.

A weak nuclear magnetic resonance generated by the precessing nuclei may be sensed by the RF coil and recorded as an NMR signal. From this NMR signal for a series of such signal acquisitions with different phase encodings, a slice image may be derived according to well-known reconstruction techniques. An overview of NMR image reconstruction is contained in the book "Magnetic Resonance Imaging, Principles and Applications" by D. N. Kean and M. A. Smith.

The RF excitation and the NMR signal may be transmitted and received, respectively, by means of one or more RF coils. Improvements in the signal-to-noise ratio of the received NMR signal can be obtained by placing "local coils" on the patient. The local coil having a smaller reception pattern can focus in on the region of interest to obtain a stronger signal and to receive less noise. A common local coil is a head coil providing for a generally cylindrical volume into which the patient's head may be placed.

During MRI, the acquired NMR signal can be thought of as filling a domain referred to as k-space. Typically, the NMR signal acquired for each different set of gradient fields completes one line of k-space data. While normally k-space data may be obtained on a row and column basis, it is also known to obtain k-space data in radial spokes through the center of k-space. After an area of k-space has been filled with data, a two-dimensional Fourier transform of the k-space data produces the MRI image.

The acquisition of each line of k-space data is preceded by the RF excitation signal described above. During this excitation, the MRI system may send the local coil a disable pulse allowing the local coil to "detune" itself electrically so as not to be overloaded by the RF excitation. This disable pulse may, for example, forward bias diodes that detune the coil.

The acquisition of the necessary k-space data is not instantaneous and requires that the patient remain substantially motionless during the acquisition period to avoid introducing artifacts into the reconstructed image. Regular physiological motion such as caused by the patient's breathing or heartbeat may be accommodated to some extent by careful selection of the gradient field order and timing. Non-periodic jerking or twitching motions, however, present a more difficult problem. Physical restraint of the patient may be impractical or distressing to the patient and only moderately successful.

SUMMARY OF THE INVENTION

The present invention provides a local coil, for example, a head coil that incorporates a motion sensor for correction of motion artifacts. The motion information may be provided directly to the MRI machine for motion correction or machine independent motion correction can be performed in which a motion threshold is detected and used to zero portions of lines of k-space data corrupted by motion or the motion signal is used to make correcting phase shifts in the k-space data before it is received by the MRI machine.

Specifically, the present invention provides a local coil for use in MRI systems and having antenna conductors fitting about a portion of a patient to detect NMR signals from the portion of a patient and a motion sensor incorporated into the local coil and detecting motion of the portion of the patient to provide a signal indicating the motion.

Thus, it is one object of the invention to provide a local coil that can detect patient motion for the purpose of correcting or avoiding image artifacts in the reconstructed MRI image.

The antenna conductors may provide a volume for receiving a patient's head and detecting NMR signals therefrom, the volume allowing movement of the patients' head therein and the motion sensor may detect motion of the patient's head within the volume.

Thus, it is another object of the invention to allow improved head imaging in cases where the patient is prone to movement.

The motion sensor may be an accelerometer attached to the patient's head.

It is thus another object of the invention to provide a compact motion sensor that may operate within the environment of a MRI machine.

The local coil may include an optical fiber and the accelerometer may provide a photovoltaic cell receiving light power from the optical fiber to produce electricity for the accelerometer. In addition, or alternatively, the local coil may include a light-emitting device transmitting the signal indicating motion as a light signal.

Thus, it is another object of the invention to provide a system for placing a motion sensor near the patient without creation of stray fields or antenna structures from power carrying conductors.

The local coil may include a processor zeroing the NMR signals when the indication of motion is above a predetermined threshold.

Thus, it is one object of the invention to provide an MRI machine independent system for correcting motion artifacts.

Alternatively, the processor may correct a phase of the NMR signal according to the motion signal.

Thus, it is another object of the invention to optionally provide more sophisticated correction of motion artifacts.

The invention can provide generally a motion artifact correction system for local coils used with an MRI machine having a motion sensor providing a signal indicating motion of a portion of a patient imaged by a local coil; and a processor system receiving the indication of motion from the motion sensor; receiving a detected NMR signal from the local coil; correcting the NMR signal based on the indication of motion; and providing the corrected NMR signal to the MRI machine.

It is thus another object of the invention to offer a coil independent motion correction system.

The invention may provide a patient motion detector for use with MRI machines having an accelerometer, a strap for attaching the accelerometer to the patient, and an optical fiber providing communication between the accelerometer and a point remote from the accelerometer.

Thus, it is another object of the invention to provide a motion detection system broadly suitable for the MRI imaging environment.

These particular objects and advantages may apply to only some embodiments falling within the claims and thus do not define the scope of the invention.

DETAILED DESCRIPTION OF THE PREFERRED EMBODIMENT

Figure 1:
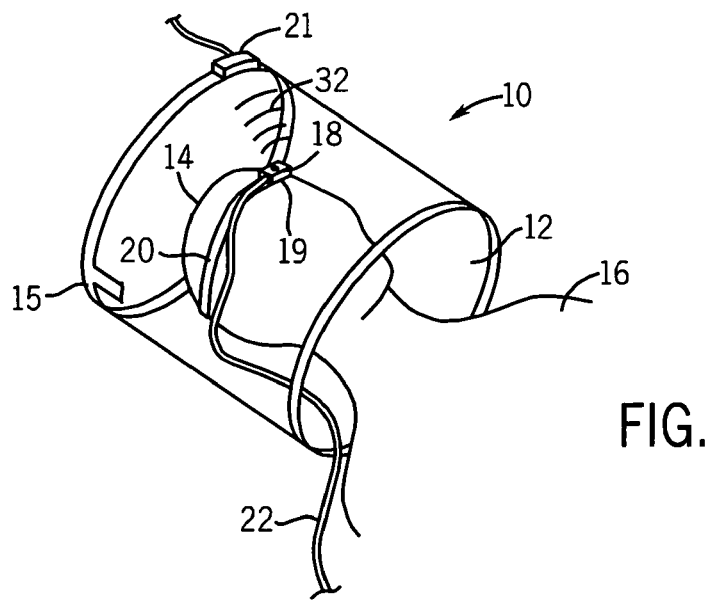
FIG. 1 is a simplified perspective view of a head coil suitable for use with the present invention, showing the positioning of the patient's head within the head coil, a headband accelerometer as fed by a fiber optic cable, and an in-coil processor receiving transmitted acceleration signals from the headband accelerometer.

Referring now to FIG. 1, a local coil 10, for example, a head coil, may provide a volume 12 into which the head 14 of a patient 16 may be placed for MRI scanning within the bore of an MRI machine (not shown). The volume 12 is defined generally by antenna conductors 15 that serve to transmit radio frequency excitation signals to the patient 16 and/or to receive NMR signals from the patient 16 as is understood in the art.

An accelerometer unit 18 may be attached to the forehead of the patient 16 by means of an elastic headband 20. The accelerometer unit 18 incorporates on its lower surface a non-slip cushion 19 to move with the patient's head 14 as retained by the elastic headband 20. A fiber optic cable 22 may pass into the volume 12 from a remote source (not shown) providing a source of light energy to the accelerometer unit 18.

Figure 2:
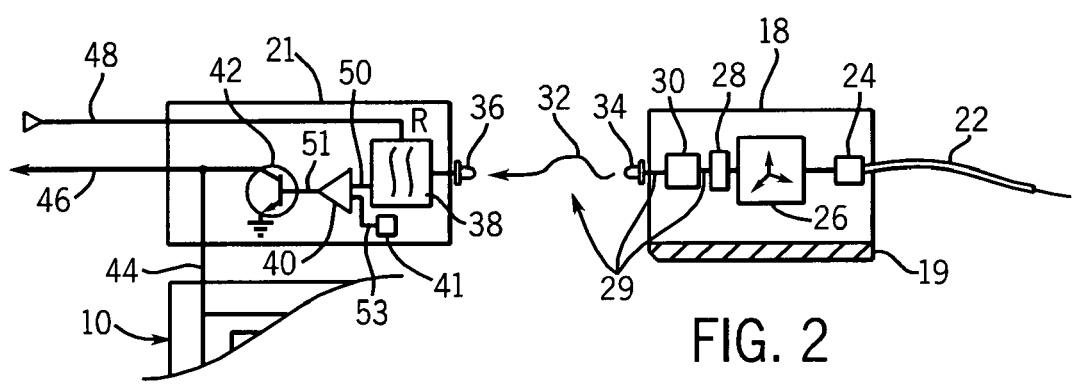
FIG. 2 is a schematic representation of the headband accelerometer showing the transmitter and in-coil receiver of FIG. 1 in a first embodiment where absolute magnitude of motion is detected.

Referring now to FIG. 2, light from the fiber optic cable 22 may be received by a photovoltaic cell 24 contained within the accelerometer unit 18 to produce a source of electrical power. The electrical power may be provided to a micro electromechanical machine (MEM) type three-axis accelerometer 26 which may measure acceleration of the patient's head 14 along three Cartesian coordinates or along the axes of yaw, pitch, and roll.

A magnitude of acceleration of the patient's head 14 may be extracted by arithmetic circuitry 28, for example in the case of the Cartesian device, by taking the square root of the sum of the square of each acceleration along each of the Cartesian coordinates. This magnitude of acceleration 29 may then be provided to an infrared transmitter 30 which may encode the magnitude signal on an infrared light beam 32 from an infrared light-emitting diode (LED) 34. A similar approach may yield a magnitude for the yaw, pitch, and roll device.

The infrared light beam 32 is of wide angle to be received at a variety of angles of the patient's head 14 by an infrared receiving diode 36 on a processor unit 21 attached to the local coil 10. Note that processor unit 21 is not a reference for the detection of motion and that the present invention can also be used in situations where the local coil 10 may move with the patient, for example, when the local coil 10 is a flexible coil wrapped about the patient 16. The processor unit 21 may be powered by electrical signals normally provided by the local coil 10 including, but not limited to, energy captured from the disable pulse from the MRI machine or by light energy delivered by a fiber optic cable 22', photovoltaic cell 24' similar to that described above.

The acceleration signal 29 received by the infrared receiving diode 36 is then provided to integrator 38 which performs two integrations on the acceleration signal to provide a motion signal 50. This motion signal 50 is then provided as one input to a comparator 40 which produces a trigger signal output 51 to a shorting transistor 42 or other solid-state switch when the motion exceeds a predetermined motion threshold 53. The predetermined motion threshold 53 may be adjustable and set by the user through a potentiometer 41 or other means well known in the art. As an alternative to a switch, the comparator may otherwise impress a voltage of zero on the NMR signal conductor 46 to the MRI machine to override the NMR signal.

The shorting transistor 42, when energized by the comparator 40, shunts the NMR signal 44 from the coil 10 to ground effectively zeroing that signal which would otherwise proceed along an NMR signal conductor 46 to the MRI machine (not shown) according to methods well known in the art.

Figure 3:
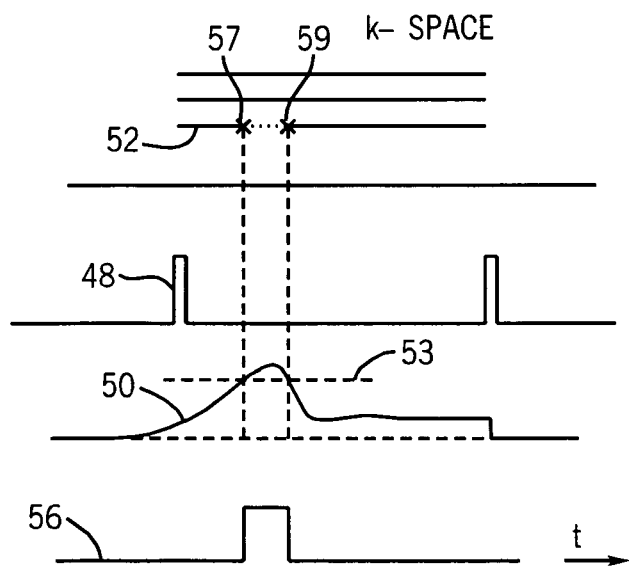
FIG. 3 is a set of time-aligned graphs plotting motion of the patient, disable pulses received from the MRI machine, the filling of a row of k-space, and motion threshold pulses used to zero k-space values.

Referring now to FIGS. 2 and 3, a disable pulse 48 from the MRI machine is received by a reset line on the integrator 38 to reset the integrator 38 to zero at the beginning of each k-space line 52. In this way, the motion signal 50 will be zeroed immediately upon the occurrence of each disable pulse 48 and afterwards will have a value equal to the amount of motion since the beginning of a k-space line 52. When the motion indicated by motion signal 50 exceeds a predetermined motion threshold 53 set by potentiometer 41, the transistor 42 is activated zeroing the k-space line 52 at that point 57 (as indicated by a dotted line). In a first embodiment, the k-space line may be "released" at point 59 if the motion signal 50 drops again below the predetermined motion threshold 53 during the current k-space line, as shown. When the k-space line 52 is released, NMR data is again recorded from point 59. In an alternative embodiment (not shown), a latch holds the k-space line in zeroed configuration until the end of the k-space line 52 regardless of further motion of the patient, the latch being set by the comparator 40 and reset by the disable pulse 48. The present inventor has determined that zeroing this k-data produces fewer image artifacts than allowing the phase shifted data to be incorporated into the image.

Figure 4:
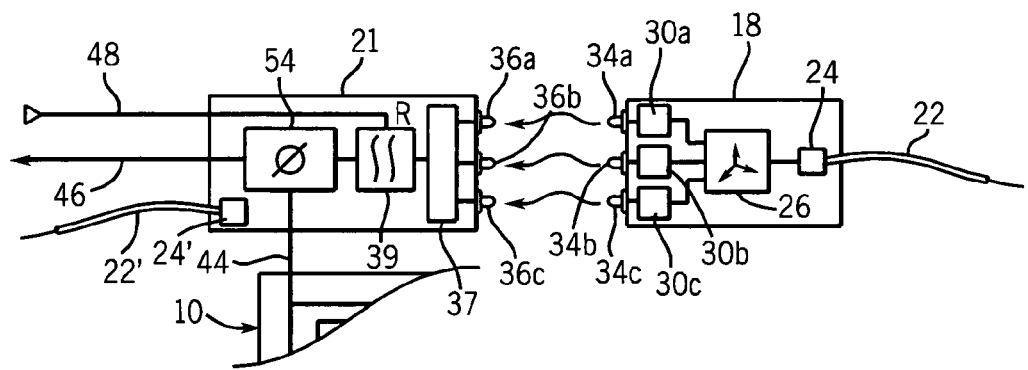
FIG. 4 is a figure similar to that of FIG. 2 showing an alternative embodiment of the invention in which direction specific motion is detected and the k-space data is corrected at the coil level.

Referring now to FIG. 4, in an alternative embodiment, the accelerometer unit 18 may provide three separate acceleration channels, each transmitted through separate transmitters 30a, 30b, and 30c, and respective light-emitting diodes 34a, 34b, and 34c to be received by separate corresponding infrared receiving diodes 36a, 36b, and 36c. Each of the acceleration channels, for example, may be as encoded with different frequencies to preserve their mutual isolation.

The signals from each of the infrared receiving diodes 36a, 36b, and 36c may be sent directly as motion channels to the MRI machine for software image correction by the MRI machine itself. This correction can determine the changed position of the patient and perform processing on the acquired k-space data to correct it geometrically for the motion of the patient. Such correction techniques may be those well understood in the art and may generally change the phase of the k-space signals, dilating them or contracting them locally to accommodate changes in patient position. Alternatively, the motion data may be used to time the data acquisitions with predicted periods of low motion, to retake data distorted by motion, or to change the gradient fields or ordering of the acquisition of k-space lines to minimize the effects of motion based on the signals from the coil.

In an alternative, self-contained embodiment as shown, the data from the accelerometer 26 may be combined by a vector extractor 39 identifying translative motion of the patient 16 along a predetermined axis, for example, along the y gradient field in which motion will create a phase shift in the k-space data. This extracted vector may generally be a trigonometric function of all of the Cartesian accelerations or may select one Cartesian acceleration mechanically aligned with the desired gradient field. In this latter case, the circuitry of FIG. 2 may alternatively be used.

The extracted acceleration is then double integrated by integrator 38 and provided to a phase shift circuit 54 which shift the phase of the NMR signal 44 from the coil 10 by an appropriate amount to counteract the motion of the patient before the NMR signal 44 is provided along NMR signal conductor 46 to the MRI machine. The disable pulses 48 may be used to reset the integrator 38 at the beginning of each k-space line or only at the beginning of the acquisition of k-space data.

While the present invention describes the use of an accelerometer to detect motion, it will be recognized that other motion detection techniques may also be used including those providing optical motion detection, for example, using cameras or the like, or those using the gradient fields themselves and coils placed on the patient to deduce position of the patient based on gradient coil signal strength. Mechanical systems and pneumatic cuffs may be used in alternative embodiments of the invention.

Figure 5:
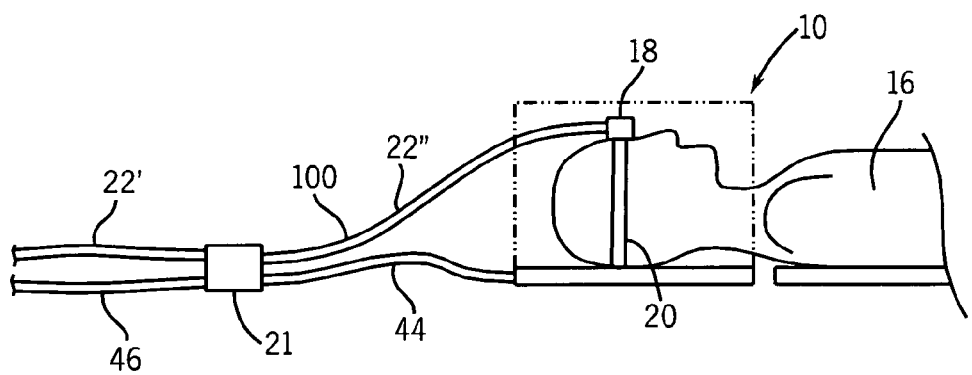
FIG. 5 is a side elevational view similar to that of FIG. 1 showing an alternative embodiment wherein the processor may be remote from the coil.

Referring now to FIG. 5, in an alternative embodiment, the accelerometer 18 may send the acceleration signal 29 over an optical fiber cable 100 directly to the processor unit 21 rather than through the air space using the light-emitting diodes 34. Power may be provided to be accelerometer 18 using a second fiber-optic cable 22" being equivalent to fiber optic cable 22 but proceeding from the processor unit 21 as a source of light power. As depicted in this embodiment, the processor unit 21 may be outside of the magnetic fields of the MRI machine and thus may receive direct electrical power or may be constructed to be placed freely within the magnetic fields and may receive its power through fiber-optic cable 22' previously described or by taping the disable pulses.

The processor unit 21 may provide, as before, either the zeroing or phase shifting correction of the NMR signal 44 as has been described above, receiving the NMR signal 44, or may in a variation provide the NMR signal 44 directly to NMR signal conductor 46 to the MRI machine thereby providing the motion signal 50 directly from the accelerometer 18 to the MRI machine without further processing service to allow software processing of the motion by the MRI machine.

It will be understood that the division of functionality, for example, the integration of the acceleration signal 29 to produce the motion signal 50 may be arbitrarily located between the accelerometer 18 and processor unit 21 or may be avoided if implemented in software of the MRI machine. Clearly, the processor unit 21 may also be attached to the coil 10 or integrated into a housing holding the accelerometer 18 when motion signals 50 are to be provided directly to the MRI machine.

It is specifically intended that the present invention not be limited to the embodiments and illustrations contained herein, but include modified forms of those embodiments including portions of the embodiments and combinations of elements of different embodiments as come within the scope of the following claims.

I claim:

1. A local coil removably insertable into a bore of MRI systems comprising:
   antenna conductors fitting about a portion of a patient to detect NMR signals from the portion of a patient; and
   a motion sensor incorporated into the local coil and detecting motion of the portion of the patient to provide a signal indicating the motion;
   whereby motion causing image artifacts may be; and
   wherein the coil further includes a processor receiving the signal indicating motion and an NMR signal from the antenna conductors to correct the NMR signal according to the signal indicating motion.

2. The local coil of claim 1 wherein the antenna conductors provide a volume for receiving a patient's head and detecting NMR signals therefrom, the volume allowing movement of the patient's head therein and wherein the motion sensor detects motion of the patient's head within the volume.

3. The local coil of claim 2 including an optical fiber and wherein the accelerometer provides a photovoltaic cell receiving light power from the optical fiber to produce electricity for the accelerometer.

4. The local coil of claim 1 wherein the motion sensor is an accelerometer attached to the patient's head.

5. The local coil of claim 4 wherein the accelerometer is attached to the patient's head by a flexible strap.

6. The local coil of claim 1 including a light-emitting device transmitting the signal indicating motion as a light signal.

7. The local coil of claim 6 including an optical fiber and wherein the light emitting device transmits the signal indicating motion over the optical fiber.

8. The local coil of claim 7 including a second optical fiber and wherein the motion sensor is an accelerometer and wherein the accelerometer includes a photovoltaic device receiving light power from the optical fiber to produce electricity for the accelerometer.

9. The local coil of claim 1 wherein the processor zeros the NMR signals when the indication of motion is above a predetermined threshold.

10. The local coil of claim 1 wherein the processor corrects a phase of the NMR signals according to the motion signal.

11. A motion artifact correction system for local coils removably insertable into a bore of an MRI machine comprising:
   a motion sensor providing a signal indicating motion of a portion of a patient imaged by a local coil; and a processor system:
   (i) receiving the indication of motion from the motion sensor;
   (ii) receiving a detected NMR signal from the local coil;
   (iii) correcting the NMR signal based on the indication of motion; and
   (iv) providing the corrected NMR signal to the MRI machine;
   wherein the motion sensor and the processor system are capable of incorporation into the local coil.

12. The motion artifact correction system of claim 11 wherein the processor zeros the NMR signal when the indication of motion is above a predetermined threshold.

13. The motion artifact correction system of claim 11 wherein the processor corrects a phase of the NMR signal according to the motion signal.

14. The motion artifact correction system of claim 11 wherein the motion sensor is an accelerometer attached to a patient's head.

15. The motion artifact correction system of claim 14 including an optical fiber and wherein the accelerometer includes a photovoltaic device receiving light power from the optical fiber to produce electricity for the accelerometer.

16. The motion artifact correction system of claim 11 including a light emitting device transmitting the signal indicating motion as a light signal from the motion detector to the processor.

17. The motion artifact correction system of claim 16 including an optical fiber and wherein the light emitting device transmits the signal indicating motion over the optical fiber.

* * * * *